(12) United States Patent
Opperman et al.

(10) Patent No.: US 11,464,599 B1
(45) Date of Patent: *Oct. 11, 2022

(54) SPECIMEN MARKING MECHANISM

(71) Applicant: MarginView, LLC, Denver, CO (US)

(72) Inventors: David Opperman, Littleton, CO (US); Robert Witkow, Denver, CO (US)

(73) Assignee: MarginView, LLC, Denver, CO (US)

( * ) Notice: Subject to any disclaimer, the term of this patent is extended or adjusted under 35 U.S.C. 154(b) by 411 days.

This patent is subject to a terminal disclaimer.

(21) Appl. No.: 16/711,653

(22) Filed: Dec. 12, 2019

Related U.S. Application Data

(63) Continuation-in-part of application No. 16/162,017, filed on Oct. 16, 2018, now abandoned, which is a continuation-in-part of application No. 15/139,012, filed on Apr. 26, 2016, now Pat. No. 10,111,727.

(60) Provisional application No. 62/162,035, filed on May 15, 2015.

(51) Int. Cl.
*A61B 90/00* (2016.01)
*A61B 90/92* (2016.01)

(52) U.S. Cl.
CPC .............. *A61B 90/39* (2016.02); *A61B 90/92* (2016.02); *A61B 2090/3987* (2016.02); *A61B 2090/3991* (2016.02)

(58) Field of Classification Search
CPC . A61B 90/39; A61B 90/92; A61B 2090/3991; A61B 2090/3987
See application file for complete search history.

(56) References Cited

U.S. PATENT DOCUMENTS

| | | |
|---|---|---|
| 4,041,931 A | 8/1977 | Elliott |
| 5,474,569 A | 12/1995 | Zinreich |
| 5,702,128 A | 12/1997 | Maxim |
| 5,902,310 A | 5/1999 | Foerster |
| 6,826,257 B2 | 11/2004 | Sayre |
| 8,301,227 B2 | 10/2012 | Phillips |
| 8,579,922 B2 | 11/2013 | Glick |
| 8,594,768 B2 | 11/2013 | Phillips |
| 9,773,168 B2 | 9/2017 | Chatow |
| 10,111,727 B2 | 10/2018 | Opperman |
| 2004/0019360 A1 | 1/2004 | Farnsworth |
| 2004/0052333 A1 | 3/2004 | Sayre |
| 2005/0234336 A1 | 10/2005 | Beckman |
| 2006/0229529 A1 | 10/2006 | Wright |
| 2007/0088362 A1 | 4/2007 | Bonutti |
| 2007/0123915 A1 | 5/2007 | Kammerer |
| 2007/0232884 A1 | 10/2007 | Maschke |
| 2007/0270681 A1 | 11/2007 | Phillips |
| 2008/0103528 A1 | 5/2008 | Zirps |
| 2009/0099588 A1 | 4/2009 | Makower |
| 2010/0187284 A1 | 7/2010 | Crainich |
| 2010/0222802 A1 | 9/2010 | Gillespie, Jr. |

(Continued)

OTHER PUBLICATIONS

Non-Final Office Action from related U.S. Appl. No. 15/139,012, dated Jan. 8, 2018.

(Continued)

*Primary Examiner* — Phong Son H Dang
(74) *Attorney, Agent, or Firm* — FisherBroyles, LLP; Craig W. Mueller

(57) ABSTRACT

According to one embodiment, an apparatus is disclosed. The apparatus includes an endoscopic clip placement tool and one or more marking clips attached to a specimen mass by the clip placement tool to mark a margin and orientation of the specimen mass.

20 Claims, 3 Drawing Sheets

(56) References Cited

U.S. PATENT DOCUMENTS

| | | |
|---|---|---|
| 2011/0082478 A1 | 4/2011 | Glick |
| 2011/0184441 A1 | 7/2011 | St-Germain |
| 2011/0301456 A1 | 12/2011 | LeClaire |
| 2014/0135773 A1 | 5/2014 | Stein |
| 2014/0276968 A1 | 9/2014 | Miksza |
| 2015/0157436 A1 | 6/2015 | Bailly |
| 2015/0374432 A1 | 12/2015 | Godara |

OTHER PUBLICATIONS

Non-Final Office Action from parent U.S. Appl. No. 16/162,017, filed Feb. 2, 2021. 12 pages.

SPECIMEN MARKING MECHANISM

This application is a continuation-in-part of pending U.S. patent application Ser. No. 16/162,017, filed Oct. 16, 2018, which is a continuation-in-part of U.S. patent application Ser. No. 15/139,012, filed Apr. 26, 2016, now U.S. Pat. No. 10,111,727, issued Oct. 30, 2018, which claims the benefit of U.S. Provisional Patent Application Ser. No. 62/162,035, filed May 15, 2015, the entire disclosures of which are incorporated by reference herein.

FIELD OF THE INVENTION

The present invention relates to medical devices, more particularly, surgical specimen margin orientation marking.

BACKGROUND

Surgical specimen margin orientation marking for endoscopic, robotic, laparoscopic, or other surgery types where body tissue is removed, is critical for pathological diagnosis, tumor excision, and other margin marking. One example of surgical specimen margin orientation marking may be featured in an endoscopic excision of a tumor. In such an example, the tumor is removed and forwarded to a pathologist for evaluation by frozen or permanent section. The pathologist subsequently performs an analysis to identify malignancy at one or more margins. A surgeon may then direct additional tissue to be excised, the orientation of which is critical for proper and accurate excision.

The current technique for surgical specimen margin orientation marking involves ink marking after a specimen has been removed from a body. FIG. 1 illustrates one embodiment of a conventional marking technique in which a specimen mass is marked with a dotted line to differentiate from surrounding tissues identifies an excised specimen mass. In such a technique an ink mark may be placed at "12:00 o'clock" position on the specimen mass.

However, this approach is inaccurate and subject to error if the orientation of the specimen is changed (e.g., dropped, manipulated, etc.). For example, it may be difficult to find the ink marks and compare to those on the removed specimen mass. Further, the surgeon, staff, or pathologist examining the specimen mass may mistakenly manipulate the removed specimen mass, or there may be miscommunication between surgeons and pathologists related to orientation. An alternative approach that may be implemented includes placement of a reference suture in the specimen at the 12:00 O'clock position. However, this approach is equally subject to error.

Accordingly, an improved surgical specimen margin orientation marking mechanism is desired. The systems and methods described herein allow for mirror image marking of multiple types of surgical specimens covering a multitude of surgeries and disciplines.

BRIEF DESCRIPTION OF THE DRAWINGS

The present invention will be understood more fully from the detailed description given below and from the accompanying drawings of various embodiments of the invention. The drawings, however, should not be taken to limit the invention to the specific embodiments, but are for explanation and understanding only.

DETAILED DESCRIPTION

A surgical specimen margin orientation marking mechanism is described. Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

In the following description, numerous details are set forth. It will be apparent, however, to one skilled in the art, that the present invention may be practiced without these specific details. In other instances, well-known structures and devices are shown in block diagram form, rather than in detail, in order to avoid obscuring the present invention.

Figure 1:
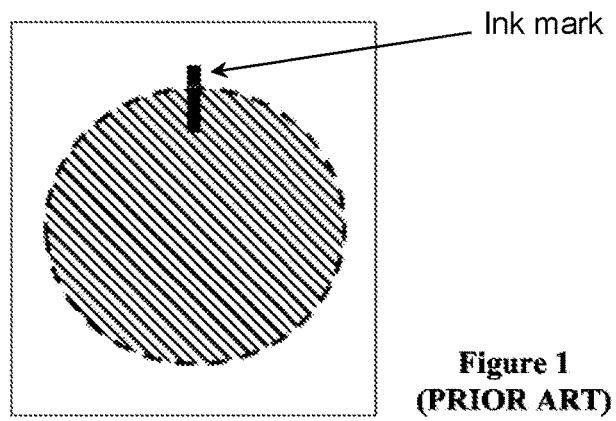
FIG. 1 illustrates a conventional surgical specimen margin orientation marking system.
Figure 2:
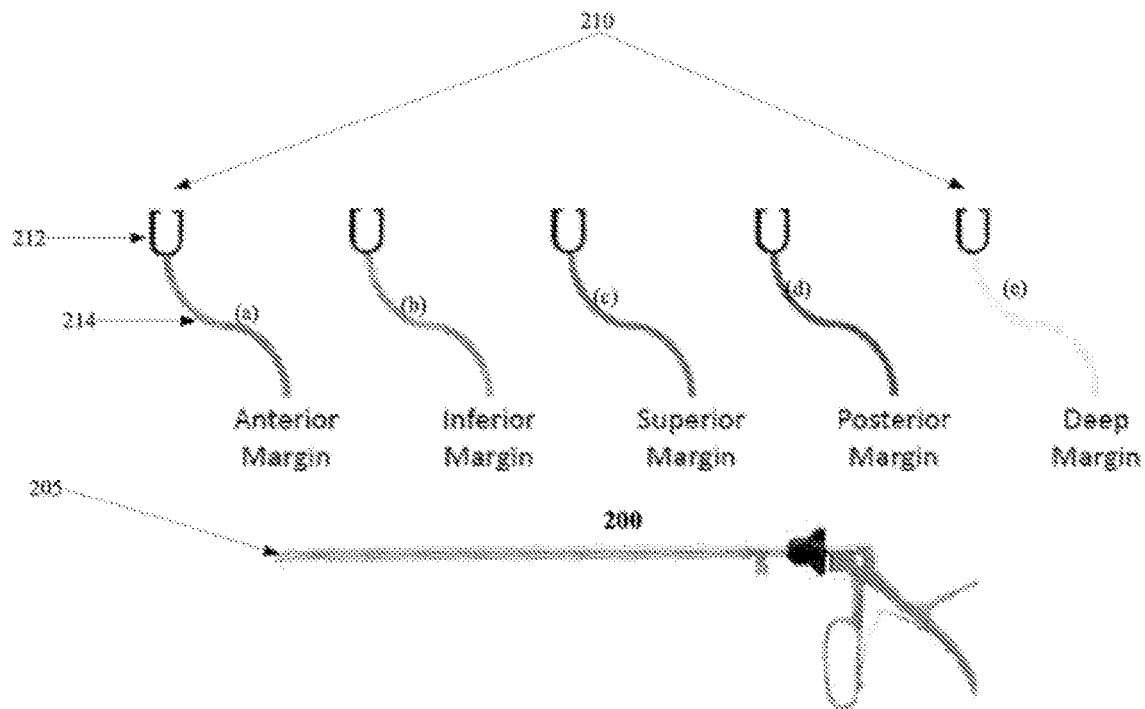
FIG. 2 illustrates one embodiment of a surgical specimen margin orientation marking mechanism.

FIG. 2 illustrates one embodiment of a surgical specimen margin orientation marking mechanism 200. Mechanism 200 includes an endoscopic clip placement tool 205 and marking clips 210. In one embodiment, each marking clip 210 includes a clip 212 and a color-coded suture 214 attached at a closed end of clip 212. In some embodiments, the clips are also color coded and match the color of the suture. In one embodiment, the clips 212 are titanium ligature clips, while the sutures are comprised of silk.

The clips and/or clip teeth may be constructed of material that suits the material to which they are to be attached—muscle, ligament, skin, fatty tissue, etc. The clips can be of any size and shape and made of any suitable material. For example, the clip's material of manufacture may be stiff, compliant, malleable, etc. to suit the surgeon's desires or to accommodate tissue character. The clips may possess a surface texture or other types of tactile or enhanced visual identification means. Further, the clips may be micro-engraved or X-ray marked with identifying information The clips can have a distinct color that identifies a predetermined location on a specimen mass. In one embodiment, the clip color coincides with that of the suture. Still further, the clips may employ microchip technology, nanotech technology, RFID technology, specialized coatings, frequency emitting devices that allows current or future-developed 3-dimensional, computer, or virtual reality medical imaging modalities to locate and identify clips in the body. These marking methods may be provided in combination or in various sub-combinations.

The sutures of some embodiments of the present invention are stiff, compliant, malleable, etc. to suit the surgeon's desires. The sutures may possess a surface texture or other types of tactile or enhanced visual identification means. Further, the sutures may be micro-engraved or X-ray identifiable with identifying information. The sutures also may employ microchip technology, nanotech technology, RFID technology, specialized coatings, frequency emitting devices that allows current or future-developed 3-dimensional, computer, or virtual reality medical imaging modalities to locate and identify sutures in the body. These marking methods may be provided in combination or in various sub-combinations.

In one example, the clips and/or sutures are configured to selectively deliver medication to the patient. That is, the aspects of various embodiments of the present invention may also allow for the utilization of adjuvant therapies that employ selective and/or controlled application of drugs, radiation, etc. In one embodiment, the clips/sutures left in the patient's body, which will be described below, employ treatment means, e.g., drug and/or radiation delivery systems controlled from an outside source. The clips/sutures of some embodiments employ drug and/or radiation delivery systems or are constructed at least partially from such systems that provide treatment over an extended period of time. For example, all or a portion(s) of the clips/sutures may comprise a drug-infused co-polymer (i.e., a polymer drug conjugate) manufactured of polylactide-polyglycolide similar to that found in dissolvable sutures.

The suture or clip may have diagnostic qualities, wherein a characteristic change occurs when conditions around the specimen mass change. For example, tumor growth, tissue DNA/RNA change, etc. would initiate a color change in the clips/sutures. The clips/sutures may also possess the ability to transmit diagnostic information outside the patient's body.

In another example, the clips and/or sutures are configured to indicate special information, e.g., distance between clips or sutures, distance between a clip and the specimen mass within the body, etc, which may assist ascertain growth of a mass. One of ordinary skill in the art will appreciate that the clips 212 may employ other types of indicia alone or in combination with corresponding indicia of the sutures 214 without departing from the scope of the embodiments of the present invention. Further, the characteristics of the clips and/or sutures do not have to match identically across the margin boundary; the primary concern is that one must later be able to correctly orient a mass, which will be described below.

According to one embodiment, the color-coded sutures 214(a)-214(e) are implemented to indicated a location. In such an embodiment, 214(a) includes a red suture indicating an anterior location. Similarly, 214(b), 214(c), 214(d) and 214(e) include green, blue, purple and yellow sutures, respectively, that represent inferior, superior, posterior and deep locations, respectively. However, other embodiments may feature various other color-coding schemes. Again, the clips can also be color-coded.

In one embodiment, a surgeon will place two marking clips 210 for specimen mass marking. In such an embodiment, one marking clip 210 is placed on a specimen mass, while the second marking clip 210 is placed in the surrounding tissue. Subsequently, a cut is made in between the two areas. The result is a mirror image marking of the two areas. That is, the paired clips allow for the specimen (ex-vivo) and the cavity created (in-vivo) to correspond to one another in mirror image fashion.

Figure 3A:
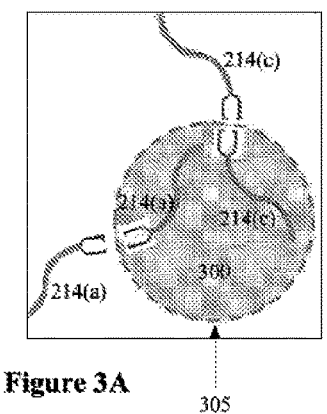
FIGS. 3A-3E illustrate embodiments of a specimen mass identified by marking clips.

Color coded sutures 214 are attached to the clips having colors designating the anterior, inferior, superior, posterior, and deep margins, as discussed above. FIGS. 3A-3E illustrate embodiments of a specimen mass identified by marking clips 210. As shown in FIG. 3A, a specimen mass 300 to be excised is identified by dotted line 305 to differentiate from surrounding tissues.

Figure 3B:
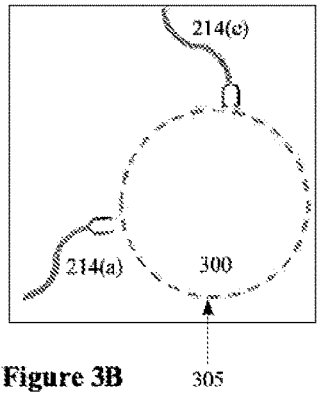
Figure 3C:
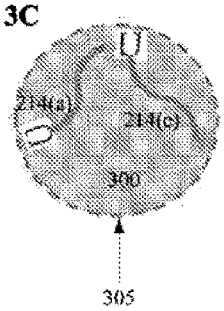

Color-coded sutures 214 devices are placed on the margins to identify orientation. For instance, clips 210 are shown having pairs of sutures 214(a) and 214(c). Note that only two types of suture 214 clips have been shown for ease of viewing. FIG. 3B shows clips 210 having sutures 214(a) and 214(b) attached to tissue above specimen mass 300 for orientation following excision of specimen mass 300, while FIG. 3C shows clips 210 having sutures 214(a) and 214(b) attached to specimen mass 300 for orientation following excision. The clips/sutures attached to tissue associated with the specimen mass can be left in the patient's body for future identification.

Figure 3D:
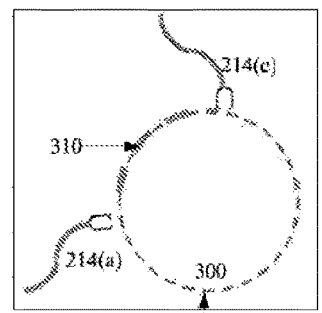
Figure 3E:
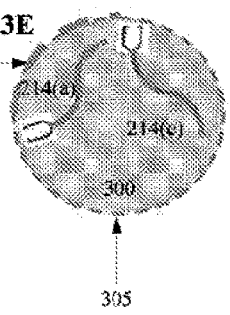

According to one embodiment, marking mechanism 200 enables accurate communication between a pathologist and a surgeon, assuming a positive or close margin determined by the pathologist. FIG. 3D shows additional tissue 310 requiring excision that can be more accurately addressed, and FIG. 3E shows a positive or close margin identified by the pathologist.

In a further embodiment, the surgeon may implement the clip 210/suture 214 combination as an effective tool for manipulating tissues, which is more efficient than attaching a handle to an otherwise slippery surface. For example, the sutures and/or clips described herein can be used to facilitate traction, counter traction, specimen mass control during robotic and laparoscopic cases, and lifting the specimen mass into extraction bags.

The clips/sutures contemplated herein may also be used to facilitate wound closure or as anchor points for implants.

Figure 4:
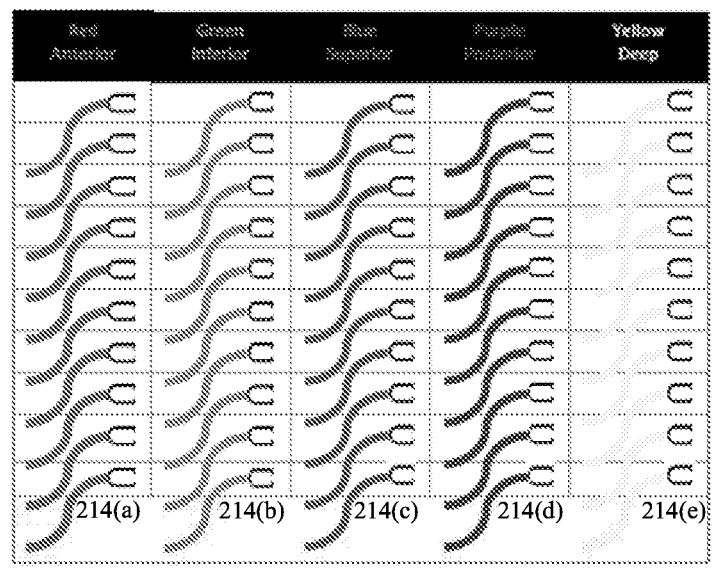
FIG. 4 illustrates one embodiment of a package of marking clips.

FIG. 4 illustrates one embodiment of a package of marking clips. As shown in FIG. 4, a package may include 25-pair/50-unit cassette of clips 210 having the various sutures 214 for endoscopic procedures.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims, which in themselves recite only those features regarded as the invention.

What is claimed is:

1. A method of marking and orienting a specimen mass with an outer margin, comprising:
   providing a first marking device adapted to attach to a first area associated with the specimen mass;
   attaching the first marking device to the first area;
   providing a second marking device adapted to attach to a second area associated with tissue surrounding the specimen mass and outside the outer margin;
   attaching the second marking device to the second area; and
   wherein the first area and the second area are located on direct opposite sides of the outer margin, such that the first marking device and the second marking device identify the orientation of the specimen mass relative to the tissue surrounding the specimen mass.

2. The method of claim 1, wherein the first marking device is configured to manipulate the mass specimen.

3. The method of claim 1, wherein the first marking device and the second marking device are not interconnected, and the second marking device remains interconnected to the second area.

4. The method of claim 1, wherein the first marking device and/or the second marking device includes a suture.

5. The method of claim 1, wherein a color of the first marking device and a color of the second marking device are identical.

6. The method of claim 1, wherein the first position is associated with an anterior area of the outer margin, an inferior area of the outer margin, a superior area of the outer margin, a posterior area of the outer margin, or a deep area of the outer margin; and wherein the second position is associates with an anterior area of the outer margin, an inferior area of the outer margin, a superior area of the outer margin, a posterior area of the outer margin, or a deep area of the outer margin, but which is different from the area of the outer margin associated with the first portion.

7. The method of claim 1, further comprising:
providing a third marking device adapted to attach to a third area associated with the specimen mass;
attaching the third marking device to the third area;
providing a fourth marking device adapted to attach to a fourth area associated with the surrounding tissue;
attaching the fourth marking device to the fourth area;
wherein the color of the first marking device and second marking device is a first color;
wherein a color of the third marking device and a color of the fourth marking device is a second color that is different from the first color; and
wherein the first marking device and the second marking device identify a first position of the specimen mass relative to the tissue surrounding the specimen mass and the third marking device and the fourth marking device identify a second position of the specimen mass relative to the tissue surrounding the specimen mass.

8. The method of claim 7, wherein the first marking device, the second marking device, third marking device, and fourth marking device each comprise an end with an associated indicator.

9. The method of claim 8, wherein the first marking device and the second marking device comprise an identical first indicator color, and the third marking device and the fourth marking device comprise an identical second indicator color.

10. A method of marking a specimen mass bounded by an outer margin, comprising:
providing a first marking device adapted to attach to a first location of the specimen mass;
attaching the first marking device to the first location;
providing a second marking device distinct from the first marking device adapted to attach to a second location associated with tissue surrounding the specimen mass;
attaching the second marking device to the second location; and
wherein the first location and the second location are positioned on direct opposite sides of the outer margin.

11. The method of claim 10, wherein the first marking device and the second marking device identify the orientation of the specimen mass relative to the tissue surrounding the specimen mass.

12. The method of claim 10, wherein the first marking device and the second marking device comprise clips.

13. The method of claim 10, wherein the first marking device is configured to manipulate the mass specimen.

14. The method of claim 10, wherein the first marking device and the second marking device are not interconnected, and the second marking device is configured to remain interconnected to the second area.

15. The method of claim 10, wherein the first marking device and/or the second marking device includes an identifier.

16. The method of claim 15, wherein the identifier is a color that corresponds to a location along the outer margin.

17. The method of claim 16, wherein the color is different if the location is associated with an anterior area of the outer margin, an inferior area of the outer margin, a superior area of the outer margin, a posterior area of the outer margin, or a deep area of the outer margin, and wherein the color associated with the anterior area is red, the color associated with the inferior area is green, the color associated with the superior area is blue, and the color associated with the posterior location is purple.

18. The method of claim 15, wherein the identifier is a suture of a predetermined color.

19. The method of claim 15, wherein the identifier is micro-engraved or X-ray marked indicia.

20. The method of claim 15, wherein the identifier is an integrated microchip or comprises nanotechnology.

* * * * *